US005196001A

United States Patent [19]

Kao

[11] Patent Number: 5,196,001

[45] Date of Patent: Mar. 23, 1993

[54] DEVICES AND METHODS FOR PREPARING PHARMACEUTICAL SOLUTIONS

[76] Inventor: Ti Kao, P.O. Box 14, Rego Park, N.Y. 11374-0014

[21] Appl. No.: 664,773

[22] Filed: Mar. 5, 1991

[51] Int. Cl.[5] .............................................. A61B 19/00

[52] U.S. Cl. ..................................... 604/416; 604/82; 604/87; 206/438

[58] Field of Search ................ 206/219, 438; 604/410, 604/416, 404, 403, 408, 409, 411, 415, 82, 86, 87; 34/240

[56] References Cited

U.S. PATENT DOCUMENTS

| | | | |
|---|---|---|---|
| 1,718,595 | 6/1929 | Smith | 604/403 |
| 2,397,051 | 3/1946 | Scherer | 604/403 |
| 2,714,974 | 8/1955 | Sawyer | 206/219 |
| 2,753,868 | 7/1956 | Seemar | 206/219 |
| 2,787,269 | 4/1957 | Cohen | 206/219 |
| 2,879,207 | 3/1959 | Poitras | 604/406 |
| 3,340,873 | 9/1967 | Solowey | 206/219 |
| 3,351,058 | 11/1967 | Webb | 206/219 |
| 3,554,256 | 1/1971 | Anderson | 604/408 |
| 3,915,212 | 10/1975 | Bujan et al. | 604/408 |
| 3,950,158 | 4/1976 | Gossett | 206/219 |
| 3,968,571 | 7/1976 | Oshatz et al. | 34/240 |
| 4,090,514 | 5/1978 | Hinck et al. | 604/142 |
| 4,147,278 | 4/1979 | Uhlig | 222/94 |
| 4,226,330 | 10/1980 | Butler | 206/219 |
| 4,265,760 | 5/1981 | Abel et al. | 604/410 |
| 4,282,863 | 8/1981 | Beigler et al. | 604/410 |
| 4,372,100 | 2/1983 | Miller et al. | 53/428 |
| 4,430,078 | 2/1984 | Sprague | 222/94 |
| 4,458,811 | 7/1984 | Wilkinson | 206/219 |
| 4,507,116 | 3/1985 | Leibinsohn | 222/95 |
| 4,602,910 | 7/1986 | Larkin | 604/410 |
| 4,610,684 | 9/1986 | Knox et al. | 604/416 |
| 4,655,763 | 4/1987 | Malcolm et al. | 604/404 |
| 4,906,103 | 3/1990 | Kao | 604/404 |
| 4,994,057 | 2/1991 | Carmen et al. | 604/408 |
| 5,005,588 | 4/1991 | Rubin | 604/52 |
| 5,102,408 | 4/1992 | Hamacher | 604/82 |

FOREIGN PATENT DOCUMENTS 0040427 11/1981 European Pat. Off. .

OTHER PUBLICATIONS

Avis et al, "Sterile Preparation for the Hospital Pharmacist", Ann Arbor Science ©1982.

Instructions from Abbott Laboratories on ADD-VANTAGE ® System container for pharmaceuticals.

Photograph of pharmaceutical container by DEY-PAK TM.

*Primary Examiner*—V. Millin
*Assistant Examiner*—Steven Wong
*Attorney, Agent, or Firm*—Lathrop & Clark

[57] ABSTRACT

A device for the preparation of sterile U.S.P. pharmaceutical solutions for intravenous use includes a transparent first bag, a transparent second bag, and a filtration unit. The filtration unit has an inlet tube and an outlet tube, the inlet tube of the filtration unit being attached to an outlet port in the first bag and the outlet tube being connected to the second bag. The first bag has a resealable inlet port through which aqueous U.S.P. solvent and unit dose holders containing medicaments may be introduced. The unit dose holders which contain ingredients to be mixed with a solvent have air-filled portions separated from ingredient containing portions by a rupturable plastic portion. The contents of the holder may be released by manipulation of the air-filled portions. The unit dose holders are labeled such that the labeling may be read through the transparent bag. The unit dose holders may be inserted in combinations within the first bag combined so that the combination of the unit dose holder ingredients can produce a near neutral pH solution when the medicaments are released into the aqueous U.S.P. solvent. The solutions produced in the first bag may then be filtered into the second bag and administered to a patient.

26 Claims, 2 Drawing Sheets

DEVICES AND METHODS FOR PREPARING PHARMACEUTICAL SOLUTIONS

FIELD OF THE INVENTION

The present invention relates to medical devices in general and devices for the preparation of pharmaceutical solutions in particular.

BACKGROUND OF THE INVENTION

Prepackaged pharmaceutical solutions are used to deliver intravenous solutions and medicines to patients for a variety of medical disorders. These solutions are commonly commercially prepared by heat sterilization methods. Often the prepared solutions will not be used immediately, thus necessitating the alteration of the pH to insure chemical stability. Prepackaged pharmaceuticals may also require preservative additives (anti-oxidants) to help preserve freshness. Glucose solutions, for example, are unstable if kept at a neutral or basic pH for long periods of time.

A problem seen with heat sterilized dextrose solutions is the formation of caramelization products of the glucose, unless the pH of the dextrose is in the range of 3-5. Acidic breakdown products, such as glycuronic acids and 5-hydroxymethylfuraldehyde, also lower the pH of the solution. Administration of solutions with the lowered pH leads to cases of post-infusion thrombophlebites. Where a buffering agent, such as sodium bicarbonate, is added to raise the pH to near physiological levels, the incidence of post infusion phlebites is decreased.

The physiological pH will vary depending on the body fluid the pharmaceutical solution is entering. For example, the arterial blood PH range is 7.38-7.44. The cerebro-spinal fluid pH range is 7.14-7.50.

Pharmaceutical solutions may need to be isotonic to prevent the net transfer of water across a membrane. Isotonicity is very important in the preparation of opthalmic pharmaceuticals. It is also known that acidic hypertonic solutions of dextrose in water are likely to cause phlebitis.

A device and method for the rapid preparation of fresh pharmaceutical solutions of known composition made from medicinal ingredients is disclosed in U.S. Pat. No. 4,906,103, incorporated by reference herein. This device includes a first bag with attached containers, a second bag, a filtration unit and a means of exerting positive pressure on the first bag. Medicinal ingredients are located in containers attached to the walls of the first bag of the device. The pharmaceutical solution is produced by adding sterile nonpyrogenic water or other suitable U.S.P. solution to the unit, snapping off the container tops from containers containing the medical ingredients needed for the medical disorder, and forcing the solution through a connected filtration unit into a second bag of the device. This apparatus advantageously allows the provision of sterile liquids prepared immediately prior to infusion and filtered rapidly enough to avoid formation of pyrogens. This apparatus includes medicinal ingredient containers fixed to the side walls of the bags which contain different ingredients suited for treatment of a variety of conditions.

It is particularly important when preparing medical solutions of precise concentrations that the containers be fully emptied into the sterile liquids and completely mixed. In harsh conditions present in poorly lit and equipped hospitals, emergency applications in the field, or in high-stress military situations, it is important that the medicinal containers be readily identifiable and easily emptied.

What is needed is a device for preparing solutions for certain medical applications which has medicinal ingredient holders which are easily and rapidly identifiable to insure that the proper medical ingredient is added to the sterile U.S.P. solution, with provision for quickly and effectively emptying the medical ingredients into the sterile U.S.P. solution.

SUMMARY OF THE INVENTION

The device for preparing sterile solutions for medicinal purposes from unit doses of pharmaceuticals of this invention has nonattached unit dose holders, a first bag with a resealable inlet port for loading the unit dose holders and the solution, a conventional in-line filtration system and a second bag for receiving the sterile pyrogen-free pharmaceutical solution. The first bag has a resealable inlet port so the bag may be loaded with and hold within it multiple unattached unit dose holders for containing pharmaceutical ingredients.

The pharmaceutical ingredients are dispensed in unit doses of U.S.P. grade chemicals and are prepackaged in unit dose holders. The dose holders are prescribed by the treating physician and can be tailored to the patient's individual needs. The unit dose holders have an upper air compartment and a lower ingredient compartment separated by a rupturable membrane. The unit dose holders have identifying labels incorporated into them and air compartments which enable the unit dose holders to float or remain suspended in the first bag when a fluid is added to the first bag through the resealable inlet port. The unit dose holders have an ingredient compartment with a rupturable end. The ingredients within the ingredient compartment are chemistries made from U.S.P. medicines or U.S.P. chemicals or concentrated liquid forms. The unit dose holder may be paired with its appropriate pH adjustment agent holder or buffering agent holder and packaged in units so that a near physiologically neutral pH solution or a solution conforming to U.S.P. standards is produced when the two unit dose holders are opened and the contents emptied into the fluid. The unit dose holders are added to the first bag through a resealable inlet port using aseptic techniques. Sterile nonpyrogenic fluid or other suitable U.S.P. solutions for the purpose of making the pharmaceutical solution may be introduced into the first bag through the inlet port. Alternatively, other solutions used for dilution of the medical ingredients may be introduced through this port. Considerations such as the tonicity of the solution may direct the choice of the ingredients chosen in order to prevent an adverse physiological reaction in the body. For example, an opthalmic preparation should be isotonic. An acidic dextrose solution should not be hypertonic in order to avoid phlebitis. The inlet port is resealable to permit sealing of the port after the unit dose holders are added.

In addition, the inlet port may be sealed off by clamping the first bag beneath the port after the unit dose holders and solution are added and before the ingredients within the holders are released into the solution. The ingredients are released from the unit dose holders by applying pressure to the holder air compartments through the sides of the first bag to rupture the membrane between the air and ingredient compartments and eject the ingredients into the sterile liquids through the rupturable end. The flexible holder may be repeatedly squeezed to insure the complete expulsion of the holder contents and the working of the holder contents off the inside walls of the ingredient compartment. The solution is mixed by manipulating the sides of the bag. A positive pressure is exerted upon the first bag or the first bag may be pulled through a wringing device which forces the solution mixture to pass through the sterilizing filter into the second bag. Sterile emergency unit dosage forms of the medicaments can be kept in the second bag or it may be left empty.

It is an object of the present invention to provide an apparatus for mixing unit doses of medicinal substances in a fluid for intravenous injection.

It is a further object of the present invention to Provide an apparatus for preparation of fresh chemistry for intravenous infusion and avoid any type of physiological harm caused by the breakdown of the chemistry products over a period of time or harm caused by lack of potency of the chemistry.

Another object of the present invention is to provide a device for loading and mixing sterile unit doses of medicinal substances in a sterile nonpyrogenic or U.S.P. suitable fluid for intravenous injection purposes.

It is also an object of the present invention to provide a container for a unit dose of medicinals which readily identifies the contents.

It is a further object of the present invention to provide a device for holding a unit dose of medicine which is easily ruptured and emptied to release all the contained medicine into a solution.

It is an additional object of the present invention to provide a simple, reliable apparatus for producing fresh, physiologically neutral, sterile solutions of medicinals for infusion, injection, irrigation and opthalmic purposes.

It is also an object of the present invention to provide a simple, reliable apparatus for producing fresh, physiologically neutral, sterile isotonic solutions of medicinals for infusion, injection, irrigation and opthalmic purposes.

It is yet another object of the present invention to provide a simple, easy-to-use method for producing fresh physiologically-neutral, sterile solutions of pharmaceuticals for infusion, injection, irrigation and opthalmic purposes.

It is a further object of the present invention to provide a simple, easy-to-use method for producing fresh physiologically-neutral, sterile isotonic solutions of pharmaceuticals for infusion, injection, irrigation and opthalmic purposes.

It is yet another object of the present invention to provide unit dose holders which are positionable in a floating or suspended position in the fluid.

It is an additional object to provide a simple-to-use pre-packaged unit dose holder filled with medicinals which can be economically transported and used under conditions where medical facilities are not available, such as under conditions of natural disaster, war, in outer space or in third world countries.

Further objects, features, and advantages of the invention will be apparent from the following detailed description when taken in conjunction with the accompanying drawings.

DESCRIPTION OF THE PREFERRED EMBODIMENTS

Figure 1:
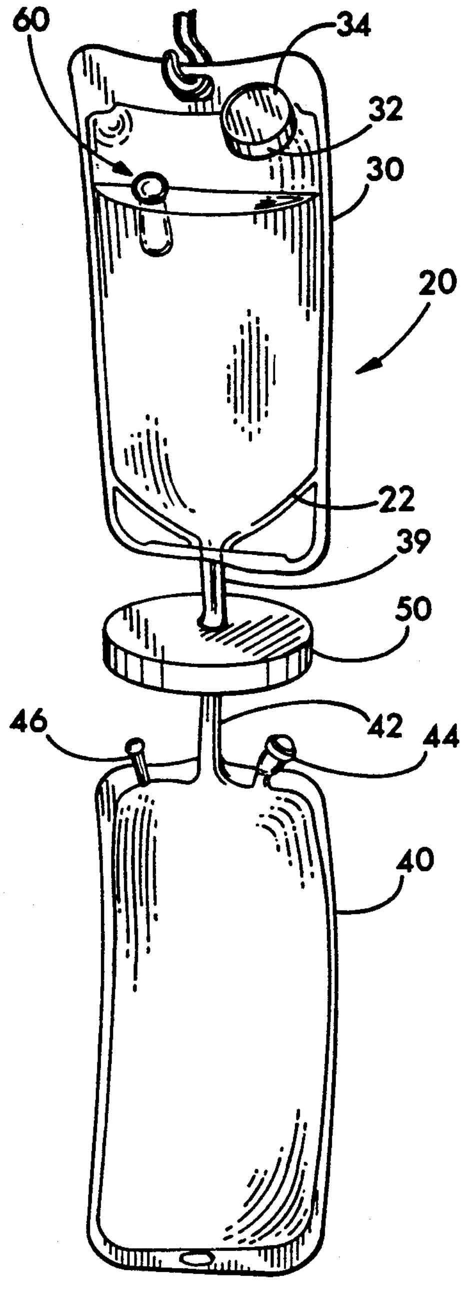
FIG. 1 is an isometric view of the medicinal preparation device of this invention having a floating unit dose holder therein.
Figure 2:
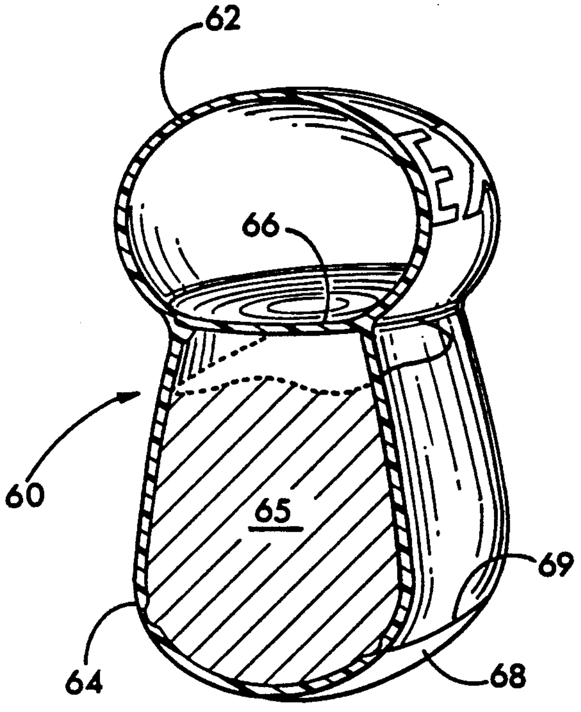
FIG. 2 is an isometric cross sectional view of the unit dose holder of FIG. 1.

Referring more particularly to FIGS. 1–8 wherein like numbers refer to similar parts, a medical device 20 for the preparation of sterile pharmaceutical solutions is shown in FIG. 1. The device includes two modified conventional plastic intravenous bags 30, 40 joined by a conventional inline filtration unit 50 which includes a coarse filter to remove particulate matter and a fine filter to remove bacteria. The device is prepackaged as a sterile unit. It is sterile on the interior and exterior, aseptically sealed in an outer wrapper. The first bag 30 has a resealable inlet port 32 and an outlet port 39 joined to the inline filter unit 50. The second bag 40 has an inlet port 42 connected to the inline filter 50 to receive fluids, an injection port 44 through which various sterile pharmaceuticals may be added, and a delivery port 46 through which sterile pharmaceutical solutions are delivered to the patient. Although not shown, the second bag may contain preloaded unit dose holders 60 filled with Pharmaceuticals. The unit dose holders 60 are preloaded into the second bag 40 by the manufacturer. The first bag 30 resealable inlet port 32 permits individual unit dose holders 60 to be loaded into the bag. As shown in FIG. 2, a unit dose holder 60 contains a known amount and composition of a medical ingredient for administration to a patient. The ingredients are preferably United States Pharmacopeia (U.S.P.) grade, Chemically Pure (CP), American Chemical Society (ACS) grade, or Association of Official Analytical Chemistry (AOAC) grade. The unit dose holders 60 contain premeasured ingredients which may be solids, such as dry powders, or liquids. The ingredients may be nutrients, electrolytes, vitamins, medicines, buffers or other medical chemistries. The buffer ingredients are premeasured for a given pre-measured medicinal and for the pH of the solvent. Each unit dose holder 60 is prepackaged as a sterile unit dose and is sterile on the exterior, and aseptically sealed in an outer wrapper. Alternatively, more than one unit dose holder 60 may be packaged together as a set. The unit dose holder may be sealed in an outer wrapping or it may be outer-wrap sealed with another unit dose holder containing a suitable acid or base neutralizing agent or other chemistry. The sterilized packaging enveloping the unit dose holders 60 are opened using aseptic techniques. The unit dose holders 60 containing medicaments prescribed for a particular patient are loaded into the first bag 30 of the device 20 using aseptic techniques. A solvent 22, such as sterile nonpyrogenic U.S.P. water, is also introduced into the first bag 30 through the resealable inlet port 32. After the unit dose holders 60 and the solvent 22 have been added, the inlet port is sealed with a threaded plastic cap 34 or any other equivalent sealing means which would create an effective seal. Once resealed, the upper portion of the first bag 30 may, in addition, be clamped to prevent backwashing through the inlet port.

As best seen in FIG. 2, a unit dose holder 60 has an air compartment 62 which is separated from an ingredient compartment by a collapsible wall 66 which is a weakened area of plastic. The ingredient compartment 64 contains the medicinal ingredients 65 intended for mixture with the solvent 22. The ingredient compartment 64 has a rupturable bottom wall 68 which forms the bottom of the compartment and is defined by a line of weakened material 69. The air compartment 62 contains air in the upper portion of the holder 60, enabling the holder to float or remain suspended upright in the solvent 22. The air compartment 62 also serves as an identifying portion 63 for displaying a label indicating the contents of a particular unit dose holder 60.

To operate the holder 60 and release the ingredients 65 into the solvent fluid 22, the walls of the air compartment 62 are pressed together forcing the collapsible wall 66 to separate and to push the contents of the unit dose holder out through the rupturable wall 68 into the fluid. The air compartment 62 acts like the bulb of an eyedropper and allows the pushing out and sucking back of fluid to wash the ingredients from the side walls of the unit dose holder 60.

Figure 3:
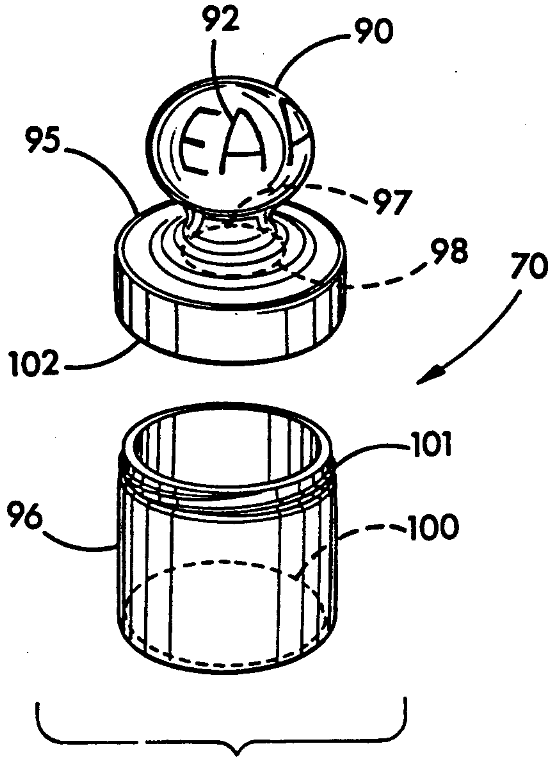
FIG. 3 is an exploded isometric view of a unit dose holder which has a screw-on top and which is adapted for use in the device of FIG. 1.
Figure 4:
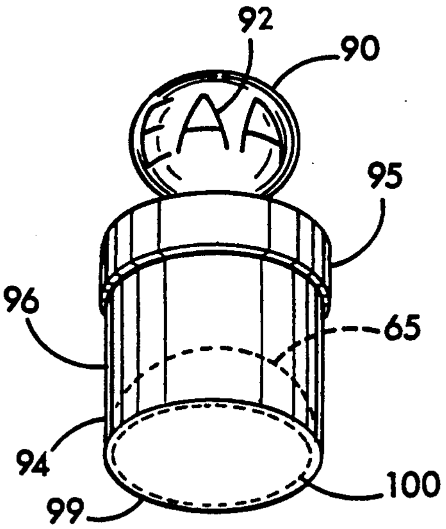
FIG. 4 is an isometric view of the assembled unit dose holder of FIG. 3.

Additional unit dose holders 70, 74, 76, 78 and 80 are shown in FIGS. 3-8. A two-part unit dose holder 70 with an air compartment molded into an identifying shape is shown in FIGS. 3 and 4. The unit dose holder 70 has an air compartment 90 which is generally spherical. Other distinctive shapes for the air compartment, such as rectangular, pyramidal, conical, or fish-tailed, may be employed to aid in rapid identification of the holder's contents. The air compartment 90 is marked with identifying indicia 92 which allow a user to ascertain the contents of the holder. The unit dose holder 70 has a collapsible wall 98 defined by a weakened area of plastic 97 which divides the air compartment 90 from the ingredient compartment 94. The ingredient compartment 94 has a rupturable bottom wall 99 which forms the bottom of the ingredient compartment 94 and is formed by a line of weakened material 100. When pressure is applied to the air compartment 90, the weakened areas of plastic 98, 100 will rupture and the ingredient 65 contained in the holder 70 will be emptied into the solvent 22.

The unit dose holder 70 is formed from an upper section 95 and a lower section 96 which are threaded together with male and female threads 101, 102. The ingredient compartment 94 of the unit dose holder 70 may thus be divided into two sections. The sections 95, 96 of the unit dose holder may be unthreaded and filled with a medicinal ingredient 65 such as a mixture of amino acid solution or with a medicinal ingredient such as an amount of dextrose sufficient to produce a 5% by weight solution of dextrose. The medicinal ingredient 65 may then be freeze-dried or lyophilized using aseptic technique. Once the medicinal is in its proper state, the two sections 95, 96 are screwed together to produce a unit dose holder 70 loaded with a desired medicinal ingredient 65.

Figure 5:
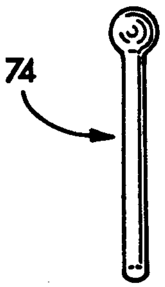
FIG. 5 is a front elevational view of an alternative unit dose holder.
Figure 6:
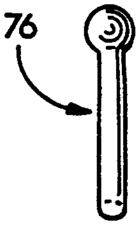
FIG. 6 is a front elevational view of another alternative unit dose holder.
Figure 7:
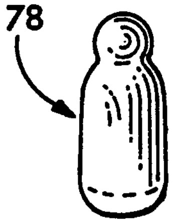
FIG. 7 is a front elevational view of yet another alternative unit dose holder.
Figure 8:
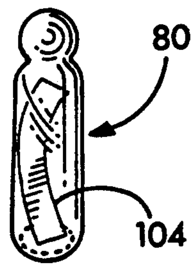
FIG. 8 is a front elevational view of an alternative unit dose holder loaded with a pH indicator strip.

A variety of shapes are possible for unit dose holders. The unit dose holder 74 shown in FIG. 5, is a narrow diameter cylinder; the unit dose holder 76, shown in FIG. 6, is a shortened cylinder; the unit dose holder 78, shown in FIG. 7, is a wider diameter cylinder; and the unit dose holder 80, shown in FIG. 8, is a wide diameter cylinder of greater capacity.

The unit dose holders can be adapted to hold an indicator for measuring pH within the ingredient compartment. The pH indicator 104 may be placed in any suitably sized unit dose holder as shown in FIG. 8.

When it is desired to intravenously administer a preparation using this invention, such as, for example, a solution of dextrose and sodium bicarbonate, first a unit dose of dextrose and then a unit dose of sodium bicarbonate for injection U.S.P. are released into the fluid by applying finger pressure to the air compartments of the unit dose holders. The chemistries and fluid are mixed by manipulating the flexible sides of the first bag 30. Sterile nonpyrogenic U.S.P. water may have a pH range of 5.0 to 7.0. Therefore, a unit dose holder with a pH indicator 104 may be added to the first bag and the holder opened after the medicinal ingredient and buffer or neutralizing agent is added to the water. The unit dose holder containing the pH indicator is opened in the manner previously described. The solution which enters the holder causes the pH indicator 104 to register. The pH of the solution can then be identified and a judgement made as to whether or not it needs to be adjusted to achieve a near physiological range. The first bag may be unsealed and another unit dose holder containing a suitable pH adjustment agent may be added as well as another unit dose holder containing a pH indicator 104. The unit dose holder may be opened and the pH adjustment agent released into the solution as described previously. Then the pH may again be tested. These steps may be repeated as necessary. The bag may then be clamped above the level of the solution to prevent backwashing and excessive pressure against the resealable entrance port 32. The mixed liquid is next forced from the first bag 30 through the outlet port 39 into the filter unit 50, through the filter unit 50, into the inlet 40 and into the second bag 40 by the application of positive pressure using a pressure device. This pressure may be applied by a conventional air pressure jacket to which a spygnomanometer pump is attached or in any equivalent way of applying positive pressure to the first bag.

For example, positive pressure may be applied by placing the bag against a flat board which is hinged to a concave shaped shell containing an air bag within the concavity. The air bag can be inflated via an external air pump, such as a bulb. The first bag containing the mixture can be inserted between the board and the concave shell and fastened securely. Squeezing the air pump bulb inflates the air bag, thus applying positive pressure on the first bag containing liquid, forcing the liquid through the filtration unit 50 into the second bag 40.

Another example of a device to apply positive pressure to the first bag is by a flat board which has two parallel rails on either side spaced the width of the bag and incorporated and fixed onto the board. A rigid device rides perpendicular to the rails. The first bag 30 is placed between the rails and the rigid device. Moving the rigid device along the length of the first bag 30 applies positive pressure to the bag, forcing the liquid in the first bag 30 through the filtration unit 50 into the second bag 40.

Alternatively, the first bag 30 can be clamped in place above the fluid level and wrung through a wringer processer which has rollers closely spaced apart and which rollers apply pressure to the sides of the bag 30 below the clamp forcing the liquid through the tubing into the filtration unit, out of the filtration unit 50 and into the tubing leading to the second bag 40. The wringer may have a conventional design with a hand crank to move the rollers.

Once the liquid has been expressed into the second bag 40, the tubing 42 to the second bag 40 is clamped off beneath the filtration unit 50 and cut.

The filter unit 50 has a conventional combination filter and removes particulate matter and bacteria.

Examples of medical ingredients contained in the unit dose holders include the following medical chemistries: Where two or more unit dose holders are described, the respective unit dose holders may be aseptically enveloped within a sterile, nontoxic, and non-allergenic enveloping material.

1. Unit Doses of Dextrose and Sodium Bicarbonate. The unit dose of dextrose contains sterile U.S.P. dextrose powder by weight in an amount sufficient to be diluted to 5% solution and a unit dose of U.S.P. injection grade sodium bicarbonate in an amount sufficient to produce a solution with a pH above 7 with the addition of sterile nonpyrogenic water.

2. Unit Doses of Amino Acid and Sodium Hydroxide. A unit dose of amino acids contains dried anhydrous amino acid such as "Nephramine" (manufactured by American McGaw Co., a division of American Hospital Supply Corporation) in an amount sufficient to form a specified strength of solution, and a unit dose of 0.1 normal NaOH solution in an amount sufficient to produce a solution of amino acids with approximately a pH of 6.5 upon the addition of sterile nonpyrogenic U.S.P. water in a quantity sufficient to make 1 liter of solution.

3. Unit dose of Amino Acid and unit dose of Glacial Acetic Acid. A unit dose of dried anhydrous amino acid such as American McGaw's Heptamine in an amount sufficient to form a specified strength of solution. A unit dose of glacial acetic acid in an amount sufficient to produce a solution of amino acids with a pH of approximately 6.5 in sterile nonpyrogenic water in a quantity sufficient to make 1 liter of solution.

4. For irrigation purposes, unit doses of Neomycin Sulfate, Polymycin and Sodium Chloride. A unit dose of Neomycin sulfate is an amount of 250 mg. A unit dose of Polymycin B sulfate is an amount of 25 mg. A unit dose of sodium chloride is an amount of 2.25 gm. These unit doses are mixed with U.S.P. water to a volume of 1 liter.

5. For opthalmic purposes, unit doses of atrophine sulfate, U.S.P. water. A unit dose of atrophine sulfate is 3 gm. A unit dose U.S.P. water is 43 ml. The unit doses are diluted with sufficient Isotonic Buffered Sorenson's Phosphate solution to make 300 ml of solution to produce a solution with a pH of approximately 6.8 and which is isotonic with body fluids.

6. Unit doses of Electrolyte. Specific quantities of anhydrous powders of U.S.P. electrolyte chemistries such as KCL, NaCl may each be placed in unit dose holders and be added to Example 1 to result in a Dextrose solution containing electrolytes.

7. Unit doses of Testosterone Propionate for injection purposes. A specific quantity of U.S.P. injection grade testosterone propionate is placed in unit dose holders. This is added to a specific amount of U.S.P. oil to form an oily solution.

It should be understood that alternate shapes and constructions of unit dose holders may be employed in connection with the device 20, and that although a screw on threaded cap is shown to reseal the first bag inlet port, alternatively seals may be provided by a snap-on cap, a stopper, a mechanical valve, or other similar elements.

It is understood that the invention is not confined to the particular construction and arrangements of parts herein illustrated and described, but embraces such modified forms thereof as come within the scope of the following claims.

I claim:

1. A device for the preparation of sterile pharmaceutical solutions comprising:

(a) a first bag having a transparent, flexible plastic lining that defines a chamber;

(b) an inlet port formed in the lining and leading to the chamber, the inlet port permitting the loading of a unit dose holder into the chamber and the admission of a solvent into the chamber;

(c) a cap which seals the first bag inlet port after the loading of a unit does holder within the chamber;

(d) an outlet port leading away from the chamber located in the lining beneath the inlet port;

(e) a unit dose holder located completely within the chamber;

(f) a filtration unit having a filter combination suitable for the filtration of bacteria and particulate matter and an inlet tube and an outlet tube, the inlet tube of the filtration unit being attached to the outlet port of the first bag; and (g) a second bag having an inlet port and an outlet port, the inlet port of the second bag being attached to the outlet tube of the filtration unit, wherein a solution contained within the first bag may be forced through the filtration unit into the second bag to form a solution adapted for medical use.

2. The device of claim 1 wherein the unit dose holder is located completely within the first bag chamber and unconnected to the first bag and containing an ingredient adapted to from a specified pharmaceutical solution when combined with a solvent admitted into the chamber.

3. The device of claim 2 wherein the unit dose holder is fabricated of a transparent plastic material.

4. The device of claim 2 wherein the unit dose holder has two sections, an upper section and a lower section, which are releasably engaged with one another to form the ingredient-filled portion.

5. The device of claim 1 wherein the unit dose holder is dimensioned to fit through the inlet port so it may be introduced into the chamber, wherein the unit dose holder has a flexible, air-filled portion spaced above a rupturable membrane, and an ingredient-containing portion located beneath the membrane, the ingredient-containing portion further having an area of weakened material located beneath the membrane portion, wherein the rupturable membrane, and the area of weakened material are susceptible to rupture upon application of pressure to the air-filled portion, wherein pressure applied to the flexible air-filled portion will cause both the rupturing of the rupturable membrane and the rupturing of the area of weakened material thus causing an ingredient contained in the holder to be released into the chamber.

6. The device of claim 5 wherein the unit dose holder has a label identifying the ingredient contained therein on the air-filled portion.

7. The device of claim 1 further comprising a means for exerting positive pressure upon the chamber of the first bag to force the pharmaceutical solution from the first bag through the filtration unit and into the second bag.

8. The device of claim 7 wherein the means for exerting a positive pressure upon the chamber is a pair of rollers through which the first bag filled with solution is pulled.

9. The device of claim 1 further comprising a unit dose holder located completely within the second bag, unconnected to the second bag and containing an ingredient adapted to form a specified pharmaceutical solution when combined with a solution admitted into the second bag.

10. The device of claim 9 wherein the unit dose holder within the second bag contains an emergency unit dose of medicine.

11. The device of claim 9 wherein the unit dose holder has a flexible, air filled portion spaced above a rupturable membrane, and an ingredient-containing portion is located beneath the membrane, wherein pressure applied to the flexible air-filled portion will cause the contents of the holder to be released into the second bag.

12. The device of claim 11 wherein the unit dose holder has a label identifying the ingredient contained therein on the air-filled portion.

13. The device of claim 9 wherein the unit dose holder is fabricated of a transparent plastic material.

14. The device of claim 9 wherein the unit dose holder has two sections, an upper section and a lower section, which are releasably engaged with one another to form the ingredient-filled portion.

15. A device for the preparation of sterile pharmaceutical solutions comprising:

(a) a first bag having a transparent, flexible plastic lining that defines a chamber, a resealable inlet port formed in the lining and leading to the chamber, the inlet port allowing the admission of a solvent into the chamber and an outlet port leading away from the chamber located in the lining beneath the inlet port;

(b) a filtration unit having a filter combination suitable for the filtration of bacteria and particulate matter and an inlet tube and an outlet tube, the inlet tube of the filtration unit being attached to the outlet port of the first bag;

(c) a second bag having an inlet port and an outlet port, the inlet port of the second bag being attached to the outlet tube of the filtration unit, wherein a solution contained within the first bag may be forced through the filtration unit into the second bag to form a solution adapted for medical use; and (d) a unit dose holder located completely within the first bag chamber unconnected to the first bag and containing an ingredient adapted to form a specified pharmaceutical solution when combined with a solvent admitted into the chamber, wherein the unit dose holder is dimensioned to fit through the inlet port so it may be introduced into the chamber, and the unit dose holder has a flexible, air-filled portion spaced above a rupturable membrane, and an ingredient-containing portion is located beneath the membrane, wherein pressure applied to the flexible air-filled portion will cause the contents of the holder to be released into the chamber, and wherein the unit dose holder ingredient-containing portion has an area of weakened material susceptible to rupture upon application of pressure to the air-filled portion.

16. A device for the preparation of sterile pharmaceutical solutions comprising:

(a) a first bag having a transparent, flexible plastic lining that defines a chamber, a resealable inlet port formed in the lining and leading to the chamber, the inlet port allowing the admission of a solvent into the chamber and an outlet port leading away from the chamber located in the lining beneath the inlet port;

(b) a filtration unit having a filter combination suitable for the filtration of bacteria and particulate matter and an inlet tube and an outlet tube, the inlet tube of the filtration unit being attached to the outlet port of the first bag;

(c) a second bag having an inlet port and an outlet port, the inlet port of the second bag being attached to the outlet tube of the filtration unit, wherein a solution contained within the first bag may be forced through the filtration unit into the second bag to form a solution adapted for medical use; and (d) a unit dose holder located completely within the second bag, unconnected to the second bag and containing an ingredient adapted to form a specified pharmaceutical solution when combined with a solution admitted into the second bag, wherein the unit dose holder has a flexible, air-filled portion spaced above a rupturable membrane, and an ingredient-containing portion is located beneath the membrane, wherein pressure applied to the flexible air-filled portion will cause the contents of the holder to be released into the second bag, and wherein the unit dose holder ingredient-containing portion has an area of weakened material susceptible to rupture upon application of pressure to the air-filled portion.

17. A buoyant unit dose holder for use within a device for preparing sterile pharmaceuticals having a bag formed of substantially transparent flexible material, the holder comprising:

(a) a first compartment containing air, the air containing compartment adapted to buoyantly suspend the holder within a liquid contained in the device bag;

(b) a second compartment which contains a medicament;

(c) located between the first compartment and the second compartment; and (d) portions of the second compartment which define a line of weakened material which surrounds a rupturable bottom wall beneath the first compartment and forming the bottom of the second compartment, wherein upon application of pressure to the air-filled first compartment through the device bag, the medicament contained in the second compartment is released into the bag of the device.

18. The unit dose holder of claim 17 wherein the unit dose holder has a label identifying the ingredient contained therein on the air-filled first compartment.

19. The unit dose holder of claim 17 wherein the unit dose holder has two sections, an upper section and a lower section, which are releasably engaged with one another to define the second compartment and to contain the medicament therein.

20. A unit dose holder for use in a device for preparing sterile pharmaceuticals formed of substantially transparent flexible material, comprising:

(a) a first compartment containing air and a second compartment adapted to contain an ingredient, the first and second compartments being separated by a flexible collapsible wall, the second compartment further having an area of weakened material susceptible to rupture upon application of pressure to the air-filled first compartment wherein, upon application of pressure to the first compartment, an ingredient contained in the second compartment will be released into the device; and (b) an pH indicator located within the second compartment.

21. A method for preparing sterile pharmaceutical solutions utilizing a device having a first bag having a resealable inlet port and a cap for sealing the inlet port and connected to a filtration unit which is connected to a second bag, comprising the steps of:

(a) inserting a holder of a sterile unit dose of a substance through the inlet port into the first bag of the device using aseptic techniques;

(b) adding sterile fluid through the inlet port into the first bag of the device using aseptic techniques;

(c) sealing the inlet port of the device with the cap;

(d) manipulating the first bag of the device to release the substance into the sterile fluid;

(e) manipulating the first bag of the device to mix the substance, and the sterile fluid to form a solution; and (f) forcing the solution through the filtration unit into the second bag of the device.

22. The method of claim 21 comprising the further step of testing the pH after mixing the solution by inserting a pH testing dose holder containing a pH indicator through the inlet port and into the first bag, resealing the entry port with the cap, manipulating the pH testing dose holder so that the solution contacts the pH testing indicator and adding further ingredients to bring the pH to a desired level.

23. A method for preparing sterile pharmaceutical solutions utilizing a device having a first bag having an inlet port and a cap for sealing the inlet port, wherein the first bag is connected to a filtration unit which is connected to a second bag, comprising the steps of:

(a) inserting a first holder of a sterile unit dose of a first substance through the inlet port into the first bag of the device using aseptic techniques;

(b) inserting a second sterile holder of a unit dose of a second substance through the inlet port into the first bag of the device using aseptic techniques;

(c) adding sterile fluid through the inlet port into the first bag of the device using aseptic techniques;

(d) sealing the entry port of the device with the cap;

e) manipulating the first bag of the device to release the first substance and second substance into the sterile fluid;

f) manipulating the first bag of the device to mix the first substance, the second substance and the sterile fluid to form a solution; and g) forcing the solution through the filtration unit into the second bag of the device.

24. The method of claim 23 wherein the second substance is an appropriate buffering agent for the first substance.

25. The method of claim 23 wherein the second substance is an appropriate neutralizing agent for the first substance.

26. The method of claim 23 wherein the first substance is dextrose and the second substance is sodium bicarbonate.

* * * * *

UNITED STATES PATENT AND TRADEMARK OFFICE

CERTIFICATE OF CORRECTION

PATENT NO. : 5,196,001

DATED : March 23, 1993

INVENTOR(S) : Ti Kao

It is certified that error appears in the above-indentified patent and that said Letters Patent is hereby corrected as shown below:

Column 8, line 25, "unit does holder" should be --unit dose holder--

Column 8, line 44, "adapted to from a" should be --adapted to form a--

Column 10, line 51, "located between the" should be --a flexible collapsible wall located between the--

Signed and Sealed this

Seventeenth Day of January, 1995

Attest:

BRUCE LEHMAN

Attesting Officer

Commissioner of Patents and Trademarks